United States Patent [19]

Yazaki et al.

[11] Patent Number: 4,767,843

[45] Date of Patent: Aug. 30, 1988

[54] MONOCLONAL ANTIBODY TO CARDIAC MYOSIN HEAVY CHAIN

[75] Inventors: Yoshio Yazaki, Tokyo; Masahito Sugi, Choshi, both of Japan

[73] Assignee: Yamasa Shoyu Kabushiki Kaisha, Chiba, Japan

[21] Appl. No.: 626,918

[22] Filed: Jul. 2, 1984

[30] Foreign Application Priority Data

Jul. 6, 1983 [JP] Japan ................................ 58-122579

[51] Int. Cl.$^4$ ..................... A61K 39/00; A61K 43/00; A61K 49/02
[52] U.S. Cl. ...................................... 530/387; 435/68; 435/172.2; 435/240.27; 424/1.1; 424/9; 436/548; 935/89; 935/93; 935/95; 935/96; 935/99; 935/100; 935/104; 935/106; 935/110; 935/107; 530/402; 530/808; 530/809
[58] Field of Search ...................... 435/68, 172.2, 240, 435/241, 948, 43; 260/112 B, 112 R; 424/85-87, 1.1, 9; 935/89, 93, 95, 96, 99, 100, 104, 106, 110; 436/548; 530/387, 402, 808, 809

[56] References Cited

PUBLICATIONS

Clark et al., J. Biological Chemistry, vol. 257, pp. 5449-5454, 1982.
Chemical Abstracts, vol. 99, 36897f, 1983.
Masaki, Journal of Biochemistry, vol. 76: 441-449 (1974).
Chizzanite et al., Journal of Biological Chemistry, vol 257, No. 4, 2056-2065 (1982).
Clark et al., Biochemical and Biophysical Research Communications, vol. 95, No. 4: 1680-1686 (1980).
Hoh et al., Journal of Molecular and Cellular Cardiology, vol. 10: 1053-1076 (1977).
Kahler et al., Nature, vol. 256: 495-497 (1975).
Yazaki et al., Circulation Research, vol. 35: 15-23 (1974).

Primary Examiner—Christine M. Nucker
Attorney, Agent, or Firm—Wenderoth, Lind & Ponack

[57] ABSTRACT

A monoclonal antibody having specificity to an isozyme of cardiac myosin heavy chain. The monoclonal antibody is useful as a reagent important for biochemical and pathological researches relating to cardiac muscles and diagnosis of myocardial infarction.

2 Claims, 4 Drawing Sheets

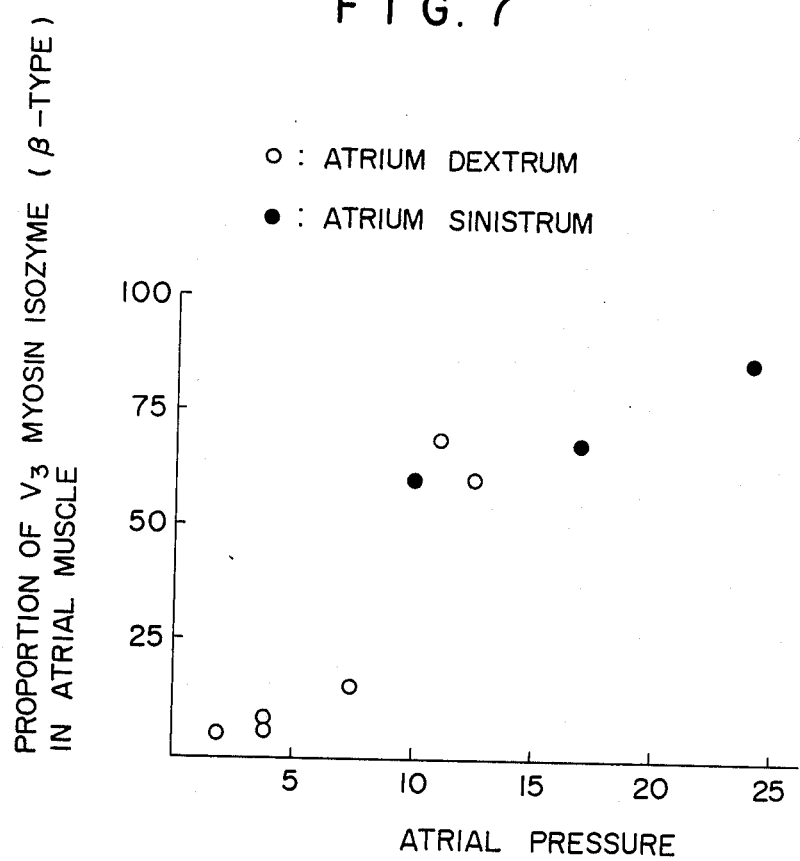

MONOCLONAL ANTIBODY TO CARDIAC MYOSIN HEAVY CHAIN

BACKGROUND OF THE INVENTION

1. Field of the Art

This invention relates to a novel monoclonal antibody having specificity to an isozyme of cardiac myosin heavy chain.

In recent years, as a method for obtaining an antibody having high specificity in a large amount, it has been known to prepare a hybridoma, by fusion of an antibody-producing cell with a myeloma cell and culturing the hybridoma thus obtained to produce a monoclonal antibody (Kohler et al, Nature, Vol. 256, p. 495 (1975)), and a large number of monoclonal antibodies have been obtained by such a method.

2. Prior Art

In the field of muscle research, antibodies against muscle proteins have long been utilized. Muscles are classified broadly into the two groups of striated muscles and smooth muscles. Striated muscles are further classified into cardiac muscles and skeletal muscles, the skeletal muscles being further cllassified into fast muscles and slow muscles. It has been reported that these can be distinguished immunochemically through the difference in immunogenicity of the myosin molecules which are major constituents of muscles (Masaki et al: J. Biochem. Vol. 76, p. 441 (1974)).

Recently, concerning also cardiac muscles, the existence of two isozymes, one being $V_1$ ($\alpha$ type) having a high ATPase activity and the other being $V_3$ ($\beta$ type) having a low ATPase activity (Yazaki et al: Circulation Research, Vol. 35 p. 15 (1974); Hoh et al: J. Mol. Cell. Cardiol. Vol. 10, p. 1053 (1978)) has become apparent. Generally speaking, in animals such as humans, bovines, canines and others, atrial muscles contain primarily $V_1$ ($\alpha$ type), while ventricular muscles contain substantially $V_3$ ($\beta$ type). Accordingly, if it is possible to prepare monoclonal antibodies specific for $\alpha$ type or $\beta$ type myosin, the atrial muscle and the ventricular muscle could be stained specifically by a method such as a biotin-avidin system. Further, these antibodies can be labelled with radioisotopes and used for localization of myocardial infarction.

W. A. Clark et al immunized mice and rats with chicken or rabbit cardiac myosin and obtained monoclonal antibodies which reacted with cardiac myosin heavy chain (Biochem. Biophys. Res. Commun. Vol. 95, p. 1680). They reported that one clone of those obtained is specific for chicken cardiac muscle and does not react with human cardiac muscle. Other two clones react with cardiac muscles of chickens, rabbits and rats, and also with human cardiac muscle, but they are also reactive with skeletal muscles and therefore not specific for cardiac muscles. These antibodies would not recognize human cardiac myosin of $\alpha$ type over $\beta$ type or vice versa.

Further, W. A. Clark et al immunized mice with chicken cardiac myosin or rabbit cardiac myosin and obtained monoclonal antibodies to cardiac myosin heavy chain $V_1$ type and cardiac myosin heavy chain $V_3$ type (J. Biol. Chem., Vol. 257, p. 5449 (1982)). However, these antibodies are shown to exhibit also cross reactivity mutually between the isozymes thereof, and nothing appears to be shown in about their specificity to human cardiac myosin.

SUMMARY OF THE INVENTION

The present invention has been accomplished under the technical background as described above and provides a monoclonal antibody having specificity to an isozyme of cardiac myosin heavy chain.

More specifically, the present invention provides a monoclonal antibody which has specificity to cardiac myosin heavy chain $\alpha$ type but does not recognize cardiac myosin heavy chain $\beta$ type and also a monoclonal antibody which has specificity to cardiac myosin heavy chain $\beta$ type but does not recognize cardiac myosin heavy chain $\alpha$ type.

The antibody of the present invention is useful as a reagent important for biochemical and pathological researches relating to cardiac muscles as described above. Further, the antibody of the present invention can be labelled with radioisotopes such as technetium-99 m, indium, etc., and applied for immunodetection, in which it is measured by whole-body gamma scintigraphy after administration into a patient, whereby localization of myocardial infarction is rendered possible. In particular, it is useful in that diagnosis of atrial myocardial infarction, which is possibly combined with ventricular myocardial infarction. It is also considered possible to detect secretion of myosin heavy chain in blood during myocardial infarction by performing immunoassay with the antibody of the invention. Thus, the antibody of the invention may also be useful for prognosis of myocardial infarction.

BRIEF DESCRIPTION OF THE ILLUSTRATIONS

In the illustrations:

FIGS. 1 through 6 are photographs taken by fluorescence microscopy of sections of human atrial muscle or ventricular muscle stained with the antibody of the present invention, in which FIG. 1 shows a normal atrial muscle stained with the antibody produced by CMA-19 cell line, FIG. 2 similarly shows a normal ventricular muscle, FIG. 3 shows a normal ventricular muscle stained with the antibody produced by HMC-14 cell line, FIG. 4 similarly shows a normal atrial muscle, FIG. 5 shows an atrial muscle of a patient with valvular disease stained with the antibody produced by HMC-14 cell line, and FIG. 6 shows an atrial muscle of a patient with valvular disease stained with the antibody produced by CMA-19 cell line, in which, the bright portions indicate the stained portions; and FIG. 7 is a graph indicating the relationship between the atrial pressure and the proportion of $V_3$ myosin isozyme ($\beta$ type) in an atrial muscle according to tissue staining with the use of the antibody of the present invention.

DETAILED DESCRIPTION OF THE INVENTION

Figure 1:
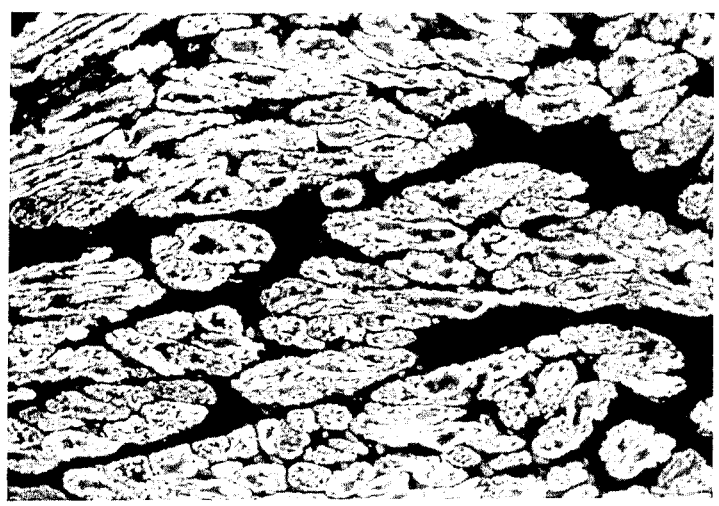

The antibody of the present invention can be distinguished from the antibodies known in the art in that it has a characteristic of being capable of recognizing an isozyme of cardiac myosin. A further useful characteristic of the antibody of the present invention is that it is capable of recognizing an isozyme of human cardiac myosin, particularly having specificity to one isozyme and not recognizing the other.

The antibody of present invention is not particularly limited in its preparation method or form of preparation, which can be selected appropriately according to the purpose. The hybridoma producing the antibody of the present invention can be obtained by applying the cell fusion method generally practiced. This cell fusion method will now be described.

(1) Preparation of antibody producing cells

Preparation of antibody-producing cells is carried out by immunizing an animal of xenogeneic species such as mouse, rat, rabbit, sheep, horse, bovine, etc., with human atrial myosin ($\alpha$ type), human ventricular myosin ($\beta$ type) or a cardiac myosin equivalent immunochemically to the human cardiac myosin $\alpha$ type or $\beta$ type prepared from bovine, horse or hog, and taking antibody-producing cells from spleen cells, thymocytes, lymphnode cells and/or peripheral blood lymphocytes.

(2) Preparation of myeloma cells

As myeloma cells, cell lines originated from various animals such as mice, rats, rabbits, and humans, can be used. The cell line to be used should preferably be drug resistant, not viable in a selective medium but viable after fusion. The cell line most commonly used is a 8-azaguanine resistant cell line, which is defective in hypoxanthine phosphoribosyltransferase and cannot be grown in hypoxathineaminoputerine-thymidine (HAT) medium. The cell line is also preferably of the "non secretor" type. Typical examples of such cell lines are $P_3$/x63-Ag 8 $U_1(P_3U_1)$, $P_3$/x63-Ag/8 6.5.3 (x63.6.5.3), $P_3$/NSI-1-Ag-4-1 (NS-1), Sp210-Ag14 (SP2) derived from mouse myeloma MOPC-21 cell line. Rat myeloma 210 RCY 3 Ag 1.2.3 (Y3 Ag 1.2.3), and human myeloma U-266-AR$_1$, and GM 1500 are also available.

(3) Cell fusion

Cell fusion may be carried out by mixing $10^7$ to $10^8$ myeloma cells with antibody producing cells at a mixing ratio of from 1:4 to 1:10 in a medium for culturing animal cells such as Eagle's minimum essential medium (MEM) and RPMI 1640. As a fusing aid, it is possible to use a polyethylene glycol (PEG) having an average molecular weight of 1,000 to 6,000, a polyvinyl alcohol, a virus, or the like.

(4) Selection of hybridoma in selective medium

Selection of hybridoma from the cells after cell fusion process can be conducted by selective growth in a selective medium. For example, the cells are diluted appropriately with, for example, RPMI 1640 medium containing 15% fetal calf serum, plated on a microtiter plate to about $10^5$-$10^6$ cells/well, a selective medium (e.g., HAT medium) is added to each well, which step is followed by appropriate exchange of the selective medium. For example, when an 8-azaguanine resistant cell line is used as the myeloma cell and a HAT medium as the selective medium, unfused myeloma cells will die on about the 10th day after cultivation, and the antibody producing cells cannot be grown in vitro for a long term. Accordingly, the cells grown on the 10th to 14th day are all hybridomas.

(5) Screening for hybridomas producing anti-cardiac myosin heavy chain $\alpha$ antibody and anti-cardiac myosin heavy chain $\beta$ antibody A screening for hybridomas producing anti-cardiac myosin heavy chain $\alpha$ antibody and anti-cardiac myosin heavy chain $\beta$ antibody was carried out according to the Enzyme Linked Immunosorbent Assay, which will be hereinafter called "ELISA".

More specifically: a cardiac myosin heavy chain $\alpha$ type such as bovine atrial myosin or a cardiac myosin heavy chain $\beta$ type such as human ventricular myosin is dissolved previously in a buffer such as phosphate buffered saline (PBS) or sodium hydrogen carbonate (pH 8.0) to 10–100 $\mu$g/ml; aliquots each of 50 $\mu$l are added to a soft plate (96 well) such as polyvinyl chloride (PVC) plate for ELISA; and the plate is left to stand at 4° C. overnight. Then, the antigen is discarded and, after washing with PBS, PBS containing 1% bovine serum albumin (BSA) is added and the mixture is left to stand at room temperature for one hour to block with BSA the sites to which no antigen is bound. Aliquots of 50 $\mu$l from the supernatant of each well are added, left to stand at room temperature for one hour, and washed three times with PBS. Then, biotinyl anti-mouse immunoglobulin serum (second antibody) is added, and the mixture is left to stand at room temperature for one hour. After washing three times with PBS, avidin D-enzyme complex is added, and the mixture is left to stand at room temperature for 15 minutes. After washing four times with PBS, the optical density is measured with addition of the substrate for the enzyme.

The well which contains a monoclonal antibody specific for the antigen can be easily judged according to the procedure as described above, whereby screening for hybridoma can be carried out.

(6) Cloning

In each well, there is the possibility that two or more species of hybridomas are contained, and therefore cloning is conducted according to, for example, limiting dilution to obtain a monoclonal antibody-producing hybridoma.

(7) Production of antibody

The most pure monoclonal antibody can be obtained by culturing the hybridoma producing said monoclonal antibody in a medium for culturing animal cells such as RPMI 1640 medium containing 10 to 15% fetal calf serum or serum free medium and obtaining the antibody from the supernatant. For the cell culturing method and conditions, those conventionally used in animal cell culturing method may be suitably applied.

On the other hand, as a method to produce antibodies in a larger amount, it is possible to employ a method in which, after a mineral oil such as pristan (2,6,10,14-tetramethylpentadecane) has been administered intraperitoneally into syngeneic animals from which the parental myeloma of hybridoma has originated, the hybridoma is injected intraperitoneally to be proliferated in a large amount therein. Hybridomas will grow as ascitic tumors within 10–18 days to produce antibodies at high concentrations (about 1 to 20 mg/ml) in serum and ascific fluid. When purification is required, purification can be carried out after ammonium sulfate fractionation by a method such as DEAE cellulose ion exchange column chromatography, affinity column chromatography using Sepharose 4B having cardiac myosin bound thereto or the like, or gel filtration column chromatography.

Examples of preferable hybridomas for producing the antibody of the present invention hitherto obtained are hybridoma CMA-19 cell line as the antibody producing cell line having specificity to the cardiac myosin heavy chain $\alpha$ type and hybridoma HMC-14 cell line, HMC-48 cell line and HMC-50 cell line as the antibody producing line having specificity to the cardiac muscle myosin heavy chain $\beta$ type.

DESCRIPTION OF THE PREFERRED EMBODIMENT

The method for preparation of these hybridomas and the properties of the antibody of the present invention are described in detail below.

I. Obtaining hybridoma

Bovine atrial myosin (1 mg/ml) or human ventricular myosin (1 mg/ml) was dissolved in a physiological sodium chloride solution and mixed with complete Freund's adjuvant in a ratio of 1:1 to prepare an emulsion. The emulsion was administered intraperitoneally into a BALB/C mouse (female, 6 weeks old) several times every two weeks (50 μg/head), and finally 30 μg of bovine atrial myosin or human ventricular myosin was administered intravenously.

Three days after the final immunization, spleen cells from the mouse were taken out and washed with MEM. Mouse myeloma $P_3U_1$ was washed with MEM and mixed with the spleen cells in a ratio of 10:1. After centrifugation, 1 ml of 50% PEG 1000 MEM solution was gradually added to a pellet or cake thus obtained to carry out cell fusion. Further, the MEM solution was gradually added to obtain a final quantity of 10 ml. Again, centrifugation was conducted, and the pellet was suspended in RPMI 1640 medium containing 15% fetal calf serum to $1 \times 10^5$ cell/0.1 ml as $P_3U_1$ and sprayed over 96-well microplate in 0.1 ml/well.

One day later, aliquots each of 0.1 ml of HAT medium were added, and, thereafter every 3–4 days, half of the medium was renewed with fresh HAT medium. On about the 7th day, growth of hybridoma was recognized in some of the wells.

Aliquots each of 50 [l of the supernatant where hybridoma was grown were added to a 96-well soft plate previously coated with bovine atrial myosin (α type) or human ventricular myosin (β type). By using avidin D-peroxidase (produced by Vector Co.) as the avidin D-enzyme conjugate, hydrogen peroxide, 4-aminoantipyrine and phenol as the substrate and the chromogenic agent, according to the ELISA method as described above, the supernatant which reacts with bovine atrial myosin but does not react with human ventricular myosin (monoclonal antibody having specificity to cardiac myosin heavy chain α type is contained in this supernatant) and the supernatant which reacts with the ventricular myosin but does not react with bovine atrial myosin (monoclonal antibody having specificity to cardiac myosin heavy chain β type is contained in this supernatant) were selected and the hybridomas were cloned by limiting dilution.

As a result, a hybridoma CMA-19 cell line producing an antibody having specificity to cardiac myosin heavy chain α type and HMC-14 cell line, HMC-48 cell line and HMC-50 cell line producing an antibody having specificity to cardiac myosin heavy chain β type were obtained.

II. Production of monoclonal antibody

Each of the hybridomas CMA-19 cell line, HMC-14 cell line, HMC-48 cell line and HMC-50 cell line was cultured in a RPMI 1640 medium containing 15% fetal calf serum in 96-well plate, then with scale-up to 25 cm² flask and 75 cm² flask, and the culture supernatants collected.

Titers of anti-cardiac myosin antibody in these supernatants were determined by the ELISA method to obtain the results shown in Table 1. The titer is expressed as dilution magnitude of the antibody sample from the original solution which gives 50% of the absorbance, taken as 100%, which is obtained by the ELISA method for the sample in which a sufficient amount of antibody exists relative to the coated antigen.

TABLE 1

| Hybridoma cell line | Titer with respect to bovine cardiac muscle myosin | Titer with respect to human cardiac muscle myosin |
|---|---|---|
| CMA-19 | 25 | — |
| HMC-14 | — | 125 |
| HMC-48 | — | 625 |
| HMC-50 | — | 625 |

These antibodies exhibited substantially no cross reactivity with human skeletal muscle.

III. Determination of subclass of antibody

A 96-well soft microplate was coated with each monoclonal antibody and, after blocking with 1% BSA containing PBS, the reactions with anti-IgA antibody, anti-IgG$_1$ antibody, anti-IgG$_{2a}$ antibody, anti-IgG$_{2b}$ antibody, anti-IgG$_3$ antibody and anti-IgM antibody were observed by means of a MONOABID EIA KIT (produced by ZYMED Co.) to determine the subclass of each monoclonal antibody.

As a result, the antibody produced by CMA-19 cell line was found to be IgG$_1$/k, the antibody produced by HMC-14 cell line to be IgG$_{2a}$/k, and antibodies produced by HMC-48 cell line and HMC-50 cell line to be IgG$_{2b}$/k.

IV. Tissue staining with the antibody of the invention

After human atrial muscle and ventricular muscle sampled during openheart surgery for valve replacement, etc., were fixed by TISSUE-TEK II (a compound used for cryostat section), sections were prepared by cryostat.

These sections were stained with the use of the antibody of the present invention according to the biotin-avidin system.

More specifically, each section was incubated with the antibody of the present invention as the first antibody in PBS (0.01M, pH 7.2) at 37° C. for 40 minutes. Then, after washing again, incubation with biotinyl anti-mouse IgG antibody (TAGO Co., used as 20-fold dilution after absorption with human liver homogenate and serum) as the second antibody was carried out similarly. Further, after washing again, incubation with fuorescein isothiocyanate labelled avidin (E.Y. Laboratories Co., used as 20-fold dilution after absorption with human liver homogenate and serum) was carried out similarly. This sample was washed and sealed with glycerine to prepare a fluorescent staining specimen.

Figure 2:
Figure 3:
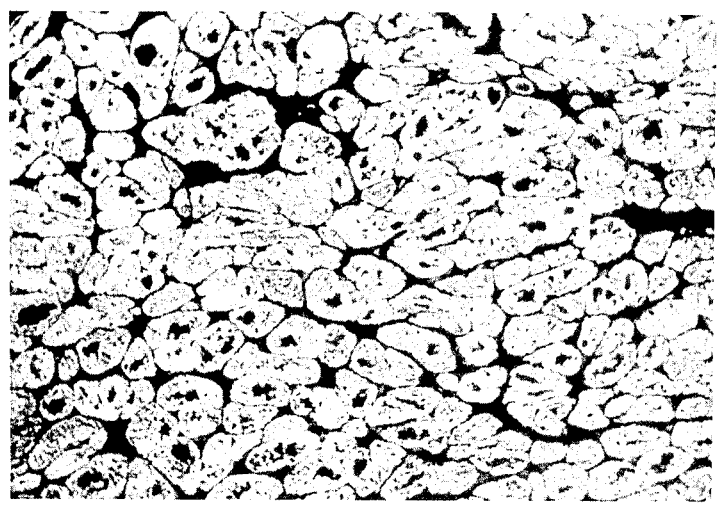
Figure 4:

These specimens were examined under fluorescence microscopy. As a result, when the antibody produced by CMA-19 cell line was used, 95 to 96% of the cells were stained in normal atrial muscle (see FIG. 1), but less than 10% of ventricular muscle cells were stained (see FIG. 2). On the other hand, when HMC-14 cell line was used, 100% of ventricular muscle cells were stained FIG. 3), but only 20 to 30% of atrial muscle cells were stained (see FIG. 4). (20–30% of normal atrial muscle existing in the form of αβ).

Figure 5:
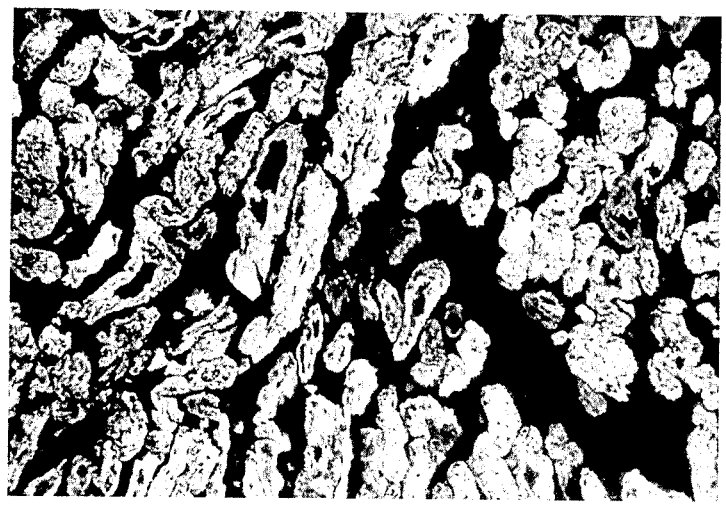
Figure 6:
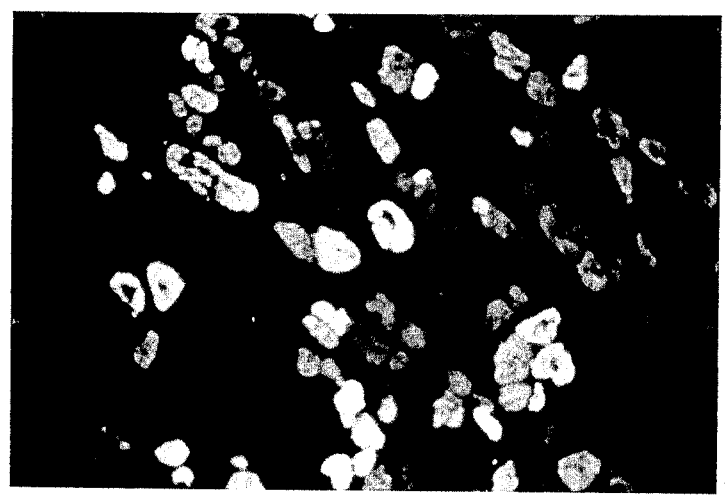

In contrast, in the cardiac muscle of the patient with valvular disease, the cells stained with the antibody produced by HMC-14 cell line in the atrial muscle increased (see FIG. 5), and the portion stained with the antibody produced by CMA-19 cell line was reduced correspondingly (see FIG. 6). This phenomenon suggests the occurrence of a isozymic change from α type to β type of the atrial myosin in valvular diseases.

Furthermore, the relationship between the atrial pressure and the ratio of V$_3$ myosin isozyme (β type) in an atrial muscle was examined by tissue staining employing the antibody of the invention, whereupon the result show in FIG. 7 was obtained. That is, in a normal atrial muscle, the atrial pressure is 5 mmHg or lower, and the content of the β type isozyme is as few as 10% or less. On the other hand, in a patient with valvular disease, the atrial pressure is 10 mmHg or higher, and the isozyme pattern of the atrial muscle myosin is reduced in α type and increased in β type.

What is claimed is:

1. A monoclonal antibody which has specificity to an isozyme of a human cardiac myosin heavy chain α-type but does not recognize an isozyme of a human cardiac myosin heavy chain β-type.

2. A monoclonal antibody which has specificity to an isozyme of a human cardiac myosin chain β-type, but does not recognize an isozyme of a human cardiac myosin heavy chain α-type.

* * * * *